US012755492B2

(12) United States Patent
Marquínez Torrecilla et al.

(10) Patent No.: US 12,755,492 B2
(45) Date of Patent: Oct. 6, 2026

(54) AUGMENTED REALITY OR VIRTUAL REALITY SYSTEM WITH ACTIVE LOCALISATION OF TOOLS, USE AND ASSOCIATED PROCESS

(71) Applicant: SEABERY NORTH AMERICA, INC., Annapolis, MD (US)

(72) Inventors: Pedro Gerardo Marquínez Torrecilla, Severna Park, MD (US); Sergio Garrido Jurado, Cordova (ES); Javier Castilla Gutiérrez, Valverde del Camino (ES)

(73) Assignee: SEABERY NORTH AMERICA, INC., Annapolis, MD (US)

( * ) Notice: Subject to any disclaimer, the term of this patent is extended or adjusted under 35 U.S.C. 154(b) by 169 days.

(21) Appl. No.: 18/020,172

(22) PCT Filed: Jul. 30, 2021

(86) PCT No.: PCT/ES2021/070582

§ 371 (c)(1),
(2) Date: Feb. 7, 2023

(87) PCT Pub. No.: WO2022/034252

PCT Pub. Date: Feb. 17, 2022

(65) Prior Publication Data

US 2023/0316669 A1 Oct. 5, 2023

(30) Foreign Application Priority Data

Aug. 10, 2020 (ES) ............................... ES202030858

(51) Int. Cl.
*G06T 19/00* (2011.01)
*A61B 1/05* (2006.01)
(Continued)

(52) U.S. Cl.
CPC .............. *G06T 19/006* (2013.01); *A61B 1/05* (2013.01); *G02B 27/0172* (2013.01); *G06V 10/761* (2022.01); *G06V 2201/07* (2022.01)

(58) Field of Classification Search
None
See application file for complete search history.

(56) References Cited

U.S. PATENT DOCUMENTS 9,230,449 B2 1/2016 Conrardy
2016/0000514 A1* 1/2016 Ellman .............. A61B 18/1442 606/1
(Continued)

FOREIGN PATENT DOCUMENTS

EP 3318361 A1 5/2018
JP 2020006419 A * 1/2020
(Continued)

*Primary Examiner* — Aaron M Richer
(74) *Attorney, Agent, or Firm* — Hayes Soloway PC

(57) ABSTRACT

An augmented reality or virtual reality (AR/VR) system with active localisation of tools, use and associated process includes an object with one or more optical markers disposed thereon; a tool; an AR/VR viewer; a first optical device of information acquisition; and a processing unit connected at least to the tool and the AR/VR viewer. Advantageously, the tool comprises a second optical device of information acquisition, in such a way that the system operates even when there are occlusions from the AR/VR viewer. The processing unit receives the information acquired by the first optical device and/or the second optical device, processes same and on the basis thereof calculates a virtual trajectory with information related to the trajectory travelled by the tool in real space.

20 Claims, 9 Drawing Sheets

(51) Int. Cl.
*G02B 27/01* (2006.01)
*G06V 10/74* (2022.01)

(56) References Cited

U.S. PATENT DOCUMENTS

| | | | | |
|---|---|---|---|---|
| 2016/0039053 | A1* | 2/2016 | Becker | G09B 19/24 228/8 |
| 2016/0267806 | A1* | 9/2016 | Hsu | G09B 19/24 |
| 2017/0046977 | A1* | 2/2017 | Becker | G09B 19/003 |
| 2018/0126476 | A1* | 5/2018 | Meess | G05B 19/182 |
| 2019/0113966 | A1* | 4/2019 | Connellan | G01C 21/1656 |
| 2019/0314040 | A1* | 10/2019 | Greenhalgh | A61B 17/7098 |
| 2019/0391372 | A1* | 12/2019 | Haverkamp | G02B 9/60 |

FOREIGN PATENT DOCUMENTS

| | | | |
|---|---|---|---|
| WO | 2016022452 | A1 | 2/2016 |
| WO | 2016144744 | A1 | 9/2016 |

* cited by examiner

AUGMENTED REALITY OR VIRTUAL REALITY SYSTEM WITH ACTIVE LOCALISATION OF TOOLS, USE AND ASSOCIATED PROCESS

CROSS-REFERENCE TO RELATED APPLICATIONS AND PRIORITY

This patent application claims priority from PCT Application No. PCT/ES2021/070582 filed Jul. 30, 2021 which claims priority from Spanish Patent Application No. P202030858 filed Aug. 10, 2020. Each of these patent applications are herein incorporated by reference in their entirety.

FIELD OF THE INVENTION

The present invention generally relates to an augmented or virtual reality system, and more specifically, to a system allowing the interaction of the user with said system by means of a tool, the latter being characterised by comprising optical means of information acquisition and by being capable of detecting itself.

BACKGROUND OF THE INVENTION

Modern virtual reality (VR) or augmented reality (AR) systems require the three-dimensional localisation (3D translation and rotation) of various objects of interest with respect to a common reference system. First, it is necessary to know the position of the user in real time in order to estimate the user's viewpoint and to be able to show suitable graphs through an AR/VR viewer. To this end, the localisation of the viewer itself in the environment must be carried out. Although augmented reality and virtual reality are generally considered to be different immersive environments, in the present invention they will be used interchangeably. Thus, any reference made to augmented reality will also be considered to refer to virtual reality, and vice versa.

In addition, many of these systems allow interaction with real objects or to use them as tools. Therefore, it is also necessary to know the location of these objects in real time and with respect to the same reference system. In many commercial systems (Oculus, HTC Vive, etc.) these objects correspond to the user's controllers that move freely and allow interaction with the virtual environment. An example of such systems is the Soldamatic solution, an AR/VR welding simulator in which a visor (welding mask), a welding part, and a welding torch or rod are located in real time.

Also known is U.S. Pat. No. 9,230,449, which discloses how an AR/VR welding training system can be designed. Knowing the relative position between the part and the torch/rod, the welding process is simulated and shown as a result of the localisation of a viewer.

The detection 3D of objects in an AR/VR system is based on the use of optical and non-optical sensors, which can be classified as follows:

a) Non-Optical Sensors

1. Electromagnetic sensors: They are based on estimating the position of the object using a magnetic field emitter and analysing the changes in the flux produced by the movement of the object. Their main problems are: reduced working area (limited to the vicinity of the electromagnetic emitter), sensitivity to interference from metallic objects in the environment, high economic cost and they do not allow a reference point to be established directly in the environment. Its advantages are its accuracy and the absence of occlusion problems.
2. Inertial sensors: They are based on the use of gyroscopes and accelerometers to know the position and rotation of an object. Their main problem is that they quickly accumulate error and are therefore not usable on their own in many applications. They also do not allow a reference point to be directly established in the environment; they are sensitive to magnetic interference, and require complex post-processing. They are normally used in combination with sensors of another type (e.g. optical). On the other hand, they are inexpensive, portable, small in size and have no occlusion problems, and they provide information on the direction of accelerations, including gravity (vertical position in the environment).
3. Mechanical sensors: They are based on the direct measurement of the position of a physical device that the user can move to different locations (e.g. arms or haptic gloves). Their main drawback is that the movements are restricted to those allowed by the physical device, so their use is very limited. Advantages are that they are robust to interference and do not present occlusion problems.

b) Optical Sensors

They are the most widespread type of sensor and are fundamental to the present invention. It is based on the use of cameras to estimate the position of objects. In systems of this type, objects are observed in the field of view of the cameras and their position is estimated by means of PnP (Perspective-n-Point) algorithms or stereo or multi-view triangulation techniques. Usually some type of optical markers are used to facilitate the detection of the object in the image (LEDs, retroreflective spheres, square printed markers, etc.). In any case, the object must be visible from the camera so it does not work when occlusions are present.

In current AR/VR systems, there are two main architectures based on where the cameras are located:

a) Cameras in Fixed Positions:

In these systems the cameras are fixed in one place in the environment, e.g. on the ceiling. This is the typical configuration of motion capture (MoCap) systems and also used in many commercial VR products (HTC Vive, early versions of Oculus, Miller Live Arc, etc.). These cameras are used both to locate the user's viewer and to locate objects or tools.

Among their main advantages, it is relevant to note:

- High precision.
- They allow a reference point in the environment to be established.
- Large and scalable workload with a larger number of cameras.
- More than one user can be detected simultaneously.

However, this architecture also has a series of limitations:

- The objects of interest must be visible; it does not allow occlusions.
- The maximum workload is limited by the coverage of the cameras.
- The cameras cannot move; the workload is stationary.
- The markers on the objects must be large enough and spaced far enough apart to be detected. It does not allow small objects.

The most precise and robust results are obtained using LEDs or the like. In these cases it is necessary to apply marker identification algorithms which can be complex.

It requires a system calibration process every time the installation is modified, i.e., every time the cameras are moved.

b) Cameras in the Viewer:

In this case, the cameras are located in the user's viewer itself. The position of the objects of interest with respect to the viewer is estimated directly. Some commercial examples are Oculus Quest, Microsoft Hololens, or Soldamatic.

This architecture offers two main advantages:

It allows greater versatility than the fixed camera system, because the cameras move with the user. In other words, the workload moves with the user.

The calibration process is performed only once.

On the other hand, it suffers from a number of drawbacks:

Precision is lower than in the fixed camera system. Detection may be affected by blurring due to motion blur or the position/angle of detection of objects of interest (especially if LED markers or the like are not used).

Objects of interest must be visible; it does not allow occlusions. This is especially problematic with cylindrical-shaped tools that are typically used perpendicular to the user (brush, welding electrode, etc.).

Markers on objects must be large enough and spaced far enough apart to be detected. It does not allow small objects. This limits the type of tools that can be detected without increasing their size to add markers.

The maximum workload is limited by the coverage of the cameras. According to the configuration it can lead to "blind spots" where there is no detection.

It only detects a single user (the one who wears the viewer).

Accordingly, there is a limitation in the AR/VR solutions available in the prior art, since the application of the tool requires the user to have in his/her field of view the region of the object on which the tool is to be applied. However, this is not always possible (e.g. when visual occlusions occur) or desirable (e.g. when the AR/VR system simulates a blind welding system for blind welding competitions). In these cases, even if the user has no view of the area to which the tool is applied, it would be highly desirable for the AR/VR system to be able to realistically simulate the result of said tool/object interaction. However, none of the systems disclosed in the prior art allow this.

In the AR/VR systems mentioned above, it is often necessary to obtain the location of an object in real time. In the case of an AR system, such an object may comprise a series of markers or keypoints that are used to establish a spatial correspondence between the real object in the physical world and the virtual object in the AR/VR system. To obtain such a spatial correspondence, Simultaneous Localisation and Mapping (SLAM) techniques are common. Camera-based SLAM processes are often referred to as Visual SLAM (VSLAM). In this case the object is represented by a map of keypoints or markers that can be detected through the cameras of the AR/VR system. The most common example is VSLAM using keypoints of the object. In this case, the camera starts operating in a completely unknown environment in which a three-dimensional map of keypoints of the object is created from a plurality of images acquired by cameras of the AR/VR system. At the same time, this map is used to position the camera within the environment. A VSLAM map typically comprises the following elements:

a) List of points (three-dimensional coordinates) of the position of the markers. These markers comprise any optical feature (e.g., keypoints, edges, corners of objects, optical markers, etc.) that can be detected with the cameras and can be located within the environment of the object.

b) Other features of the markers, for example, colour, descriptors, direction of the normal, etc.

c) Keyframes, which comprise those keyframes or key images in which the markers used for generating the map of the object are observed. Said observations can be reused when the map is to be updated.

The VSLAM process executing the AR/VR system typically comprises three main steps: initialisation, localisation, and mapping, which will be discussed in detail below.

1) Initialisation: This step is only executed when the map is empty, to generate the first markers. A particular embodiment for carrying out the initialisation in the case of VSLAM with keypoints comprises capturing the same region comprising the object from at least two viewpoints. In this way, the initial position of the keypoints of the object can be triangulated and these keypoints of the object will be tracked to detect further positions of the object.

2) Localisation: This step is executed in each frame of the algorithm, for the purpose of obtaining the location of the camera or cameras of the system. Said process in turn comprises:

Locating the markers within the frame.

Searching for correspondences of the markers in the frame with the markers stored in the map.

Obtaining the position of the camera with respect to the map by mathematical optimisation and using said correspondences.

3) Mapping: This step is usually computationally expensive and is not executed on all the frames. Moreover, it is usually executed in the background so as not to interfere with the operation of the AR/VR system. In particular, it is only executed on those frames of the object that are decided to be added as a new keyframe to the map. There are many criteria for deciding whether or not to add a keyframe to said map, for example, based on whether it adds new information to the map or whether a minimum number of frames have elapsed since the last keyframe was added to the map. The higher the number of keyframes, the more complete the map is. However, the process of updating the map will also be slower and mapping and localisation procedures will require more computational resources. Therefore, it is usual to reach an intermediate point where keyframes are added only if they provide significant information. Every time a keyframe is added to the map, the map is updated, which usually involves doing the following:

Adding new markers to the map.

Deleting erroneous or outdated markers of the map.

Recalculating the position of the markers of the map based on the new keyframe and the previous keyframes.

Said SLAM process may be customised based on the specific AR/VR system or application for which it is intended.

BRIEF DESCRIPTION OF THE INVENTION

The present invention is comprised in systems for three-dimensional localisation of objects in augmented reality (AR) or virtual reality (VR) systems and allows overcoming the limitations of the aforementioned prior art. The proposed system allows knowing in real time the 3D position and rotation of an object relative to a common reference system.

As mentioned in the previous section, there is a need in the prior art for an AR/VR system with camera and viewer architecture that is robust to occlusions and allows for realistic simulation of tool-object interaction in a region beyond the region visible from the AR/VR viewer worn by the user. While the invention will primarily refer to personal viewers, such as glasses, or AR/VR headsets, any monitor or screen (e.g., screen of a computer, mobile device, tablet, or television) that allows the AR/VR environment to be represented will also be considered as being included within the scope of this term.

More specifically, a main object of the present invention relates to an AR/VR system operable by a user, wherein said system comprises:

- an object comprising one or more optical markers disposed thereon;
- a tool suitable for use by the user, occupying a position or travelling a real trajectory in a space;
- an AR/VR viewer, suitable for use by the user.
- a first optical means of information acquisition, preferably located in the AR/VR viewer;
- a processing unit connected at least to the tool and the AR/VR viewer. Said processing unit comprises the necessary hardware/software means which a person skilled in the art can recognise (one or more central processing units or CPUs, one or more graphic processing units or GPUs, one or more servers, one or more mobile applications, etc.) and the necessary connections (wired connections, wireless connections, etc.).

Said system is advantageously characterised in that:

- the tool comprises a second optical means of information acquisition.
- the optical markers comprise first markers encoded with optical information suitable for acquisition by the first optical means, and second markers encoded with optical information suitable for acquisition by the second optical means; and
- the processing unit comprises software/hardware means configured to receive the information acquired by the first optical means and/or second optical means, process said information and calculate a virtual trajectory comprising information related to the occupied position or the real trajectory travelled by the tool in space.

The tool preferably comprises the second optical means of information acquisition, which enables it to actively locate itself; whereas the first optical means of information acquisition comprise passive cameras for detecting the object. In this way, the system is especially optimised for those situations in which the use of a tool interacting on another object is to be simulated. For example, a welding torch/rod on a part, a brush on a canvas, an industrial paint sprayer, or a scalpel on a body.

In preferred embodiments of the AR/VR system, this further comprises a virtual stroke represented in the AR/VR viewer from the virtual trajectory calculated in the processing unit.

In advantageous embodiments of the system, the tool comprises third optical markers equipped with optical information suitable for acquisition by the first optical means. In this way, the system can locate the tool when said tool is not facing the object.

In particular embodiments of the system, the second optical means comprise an endoscopic camera housed in the tool. The advantage of the endoscopic camera is that it is very compact and readily moulds to tools of any type, particularly those with a cylindrical shape.

In other embodiments of the system, the tool comprises at least one actuator connected to the processing unit. Said actuator thereby allows acquiring more additional information besides the trajectory travelled by the tool, for example, the actuator can be sensitive to the force applied by the user to press it or to the pressing time. Other alternative embodiments comprise a plurality of actuators in the tool.

In some particular embodiments, the first optical means and/or the second optical means of the system comprise one or more cameras.

In preferred embodiments of the system, the tool further comprises one or more non-optical sensors to improve its precision and robustness. For example, the tool can incorporate inertial sensors, haptic sensors, thermal sensors, mechanical sensors, electromagnetic sensors, etc.

In certain embodiments of the system, the optical markers (both those placed on the object and those located on the tool) comprise artificial markers such as LEDs, QR codes, barcodes, retroreflective spheres, and/or printed markers (of any geometric shape: flat markers, square markers, circular markers, etc.); as well as natural markers such as keypoints of the object and/or tool (for example, the corners of the objects can be used as keypoints). In this sense, "encoded information" shall be understood to mean any optical information associated with or comprised in the object, naturally or added thereto, which can be captured by the optical means of acquisition and analysed by the processing unit.

In a preferred embodiment of the invention, the viewer is housed in a welding mask; the tool comprises a welding torch and/or material supply elements. Said material supply elements preferably comprise welding rods or welding electrodes. Furthermore, the object comprises a part on which the application of a welding consumable is simulated at the points delimited by the virtual stroke. In this way, the invention discloses an AR/VR simulator suitable for didactic use in welding and even in blind welding.

In alternative embodiments, the tool comprises an industrial paint sprayer, a scalpel, or haptic gloves. In this way, the invention can be applied in didactic simulators in various fields, such as welding, painting, and medicine.

In other embodiments, the tool comprises a robotic arm. In this way, the system can be used for the simulation of industrial processes, high-precision surgical procedures, or any other application requiring the use of said robotic arm.

In certain embodiments of the system, the tool can be physically connected or coupled to a termination (for example, as a casing, mouthpiece, or hood) adapted for housing the second optical means (for example, the endoscopic camera). In this way, the termination will at least partially house a portion of the tool. Preferably, the termination is adapted for being coupled to the tool permanently or temporarily (for example, by means of a thread mechanism, which allows the termination of the tool to be interchanged). The geometry and dimensions of the termination are adapted to the specific application for which the tool is used (whether it is for welding, painting, etc.).

In even more preferred embodiments, the termination further comprises third optical markers encoded with optical information suitable for acquisition by the first optical means.

Alternative embodiments of the system described above further comprise a vibration module adapted for generating various vibration patterns of the tool based on the configuration of said tool. For example, if the tool simulates a welding torch, the vibration module can generate several welding patterns defined at least by these parameters: vibration frequency, vibration intensity, and duration of the vibration. These patterns depend on the configuration of the tool and on the type welding that is simulated. The operation performed by the user with the tool (for example, a weld made on a virtual part) will be compared with the reference operation that should have been performed if said user were an expert. Based on the deviation with respect to the reference, the vibration will change in intensity, frequency, duration, or any other parameter. The vibration module comprises a sound box or any type of electronics (for example, a microcontroller, a printed circuit board, or other hardware) which allows the simple integration thereof in the tool.

As mentioned, the main field of interest relates to AR/VR simulators in which it is necessary to locate tools in order to simulate interaction between objects. Simulators of this type are especially useful in the academic field because they allow practicing and learning processes that require manual skills with the corresponding advantages of AR/VR (savings in material, unlimited practice sessions, gamification, secure environments, etc.).

A preferred use of the system of the invention consists of welding or blind welding AR simulation. In other preferred embodiments, the system is suitable for use in painting, surgery, or dentistry AR/VR simulators. In alternative embodiments, use thereof could be extrapolated to any other context, beyond AR/VR, which requires precise localisation between two objects.

It is also part of the patent the process for operating the system described above, intended for the calculation of a virtual trajectory in AR/VR systems and characterised in that it comprises performing the following steps:

- localisation of the object and the tool from the first means and/or the second optical means.
- acquisition, by means of the first optical means and/or the second optical means, of information based on the tracking of the markers of the object and on the trajectory travelled by the tool in space.
- processing of said information in the processing unit to calculate a virtual trajectory.
- periodically repeating the above steps. The update time after which the process is repeated depends entirely on the application. In some applications a continuous or real-time update of the virtual stroke is required, while in other applications this update can be adjusted at the discretion of the user.

In other embodiments of the process, wherein the localisation of the tool of the process further comprises the detection of the third optical markers. In this way, the localisation of the tool can be refined using this additional information.

In other advantageous embodiments of the invention, the acquisition step comprises capturing additional information of the tool through at least one actuator. Said actuator can be a trigger, button, or the like that is sensitive to time and to the force with which the user acts on the tool, this information being relevant for generating the virtual trajectory.

In preferred embodiments of the process, said process comprises the estimation of the position between the AR/VR viewer and the object, the position between the tool and the object, and the position between the AR/VR viewer and the tool.

For the estimation of those positions, simultaneous localisation and mapping, or SLAM (VSLAM), techniques are used in some embodiments. Preferably, said mapping is executed in real time and in parallel to the main simulation executed by the AR/VR system. In these embodiments, the system further comprises a detection module for detecting optical markers placed on the object and/or in its environment. In turn, said AR/VR system comprises processing means (for example, a computer) adapted for detecting, processing, and storing the information about the position of said optical markers. The localisation of the markers of the object and the comparison with the initial map of markers allows establishing the viewpoint between the AR/VR viewer and/or the tool with respect to the object, with a common reference frame.

The purpose of SLAM in the process of the invention comprises:

- If there is already an initial map of the markers in the object, SLAM is used to correct the positions of those markers (for example, due to said markers poorly adhering to the part). SLAM also allows adding new markers not found in the initial map. For example, in the event that there is already a map of markers, the position of said markers is corrected and keypoints are further added by applying SLAM.
- If there is no initial map, SLAM allows creating a first version.

Lastly, it should be noted that the strengths of the system object of the invention are the following:

- Precision is not affected by the movement of the viewer or by the angle/distance from which the tool is observed. In other words, precision is independent of the user's viewpoint.
- The tools on which the camera is positioned does not necessarily require optical markers for being detected, so objects with a much smaller size can be detected.

Furthermore, the invention features the advantages characteristic of optical systems with cameras in the viewer, such as:

- The workload moves with the actual user.
- They allow establishing a reference point in the environment.
- The calibration process is performed only once.
- There are no interferences due to the presence of other objects.
- Low computational processing.
- Low economic cost.

The aforementioned advantages are met when the tool observes the second optical markers of the base object. When the tool exits said field of view, the tool could continue to be detected (if desired) by means of the operation of the standard optical system with cameras in the viewer, provided that the tool itself has optical markers. For example, if a brush painting on a canvas is to be simulated, a camera would be placed on the brush and optical markers would be placed on the canvas. When the camera on the brush is facing the canvas, the relative position of the brush can be known independently of the viewer of the user. However, when the brush is not facing the canvas, it is not possible to locate it with the camera incorporated therein. In this case, the cameras of the viewer worn by the user would have to be used.

It should be noted that the situation in which the interaction of a tool on another object is to be simulated is a fairly usual process in many tasks that are susceptible to be simulated by means of AR/VR (for example, an industrial paint sprayer on a part, a brush on a canvas, a scalpel on a body, a welding torch on a part, etc.).

In summary, the invention discloses an AR/VR system comprising cameras in an AR/VR viewer, the main advantage of which is that it is not affected by occlusions because there is another camera located on the actual tool used for interaction with the object. In particular, as a result of the invention the objects and/or tools do not have to be visible from the viewpoint of the user. In this way, said objects/tools can be detected independently of the position of the viewer; i.e., there are no problems of occlusion or blind spots. In fact, it is possible to interact with the tool without there being an AR/VR viewer, although it is understood that this viewer is necessary to be able to observe the results of the simulation at any time.

Throughout the text, the word "comprises" (and derivatives thereof) must not be understood in an exclusive manner, but rather must be understood in the sense that they allow the possibility that what has been defined may include additional elements or steps. Furthermore, in the scope of the invention when reference is made to "optical" means, it is not intended to be limited to the "visible" electromagnetic spectrum, but rather any portion thereof can be used (ultraviolet, infrared, etc.). Likewise, the concept of "optical information" will be understood to mean any element that comprises encoded information that can be read or acquired by optical recognition means. Said optical information may, therefore, be encoded in a plurality of physical media (including QR codes, LEDs, images, characters, barcodes, retroreflective spheres, printed markers, etc.) provided that the recognition or reading thereof can be performed by optical means (for example, a camera). Moreover, when reference is made to a "camera", said name is not limiting, in such a way that it would be equivalent to any device capable of acquiring information in image and/or video form. Likewise, when reference is made to a "real" trajectory, reference is made to the fact that it is a trajectory in real physical space, whereas a "virtual" trajectory makes reference to a trajectory in virtual or augmented reality space. There is a relationship between both trajectories, but they are not necessarily the same.

DESCRIPTION OF THE FIGURES

To complete the description of the invention, a set of figures, which are an integral part of the description and illustrate a preferred embodiment of the invention, is provided. Said figures are to be interpreted in illustrative and non-limiting manner and are described in detail below.

The mentioned figures are accompanied by a series of reference numbers, corresponding to the following elements:

(1) Object (part).
(2) Tool (welding torch, industrial paint sprayer, scalpel, haptic gloves, etc.).
(3) AR/VR viewer.
(4) First optical means of information acquisition (in the viewer).
(5) Processing unit.
(6) Second optical means of information acquisition (in the tool).
(7) First optical markers on the object (for the viewer).
(8) Second optical markers on the object (for the tool).
(9) Third optical markers on the tool.
(10) Actuator in the tool (trigger or the like).
(11) Front end or tip of the termination.
(12) Printed circuit board with built-in lighting means.
(13) Main body.
(14) Rear end or rear cover of the termination.
(15) Hollow sheath or conduit for housing the second optical means of information acquisition.
(16) Vibration module, comprising a wired vibrating element.
(17) Actuator (trigger) of the tool.
(18) Connectors and wiring of the endoscopic camera.
(19) Printed circuit board for the second optical means (the endoscopic camera).
(20) Fixing elements (set screws, etc.).

DETAILED DESCRIPTION OF THE INVENTION

Figure 1:
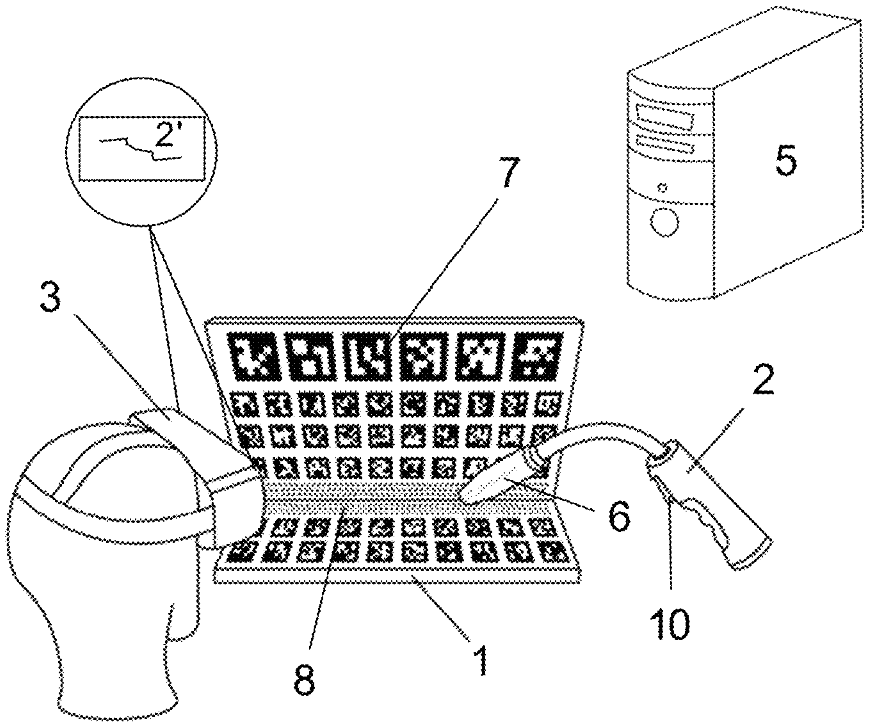
FIG. 1 shows the preferred embodiment of the invention in which the tool is a welding torch, comprising an endoscopic digital camera. It should be noted that the virtual stroke is represented on the screen of the viewer, in this case in real time, although the frequency with which the simulation is shown can be adapted based on the performance of the hardware/software means of the camera and the processing unit.
Figure 2:
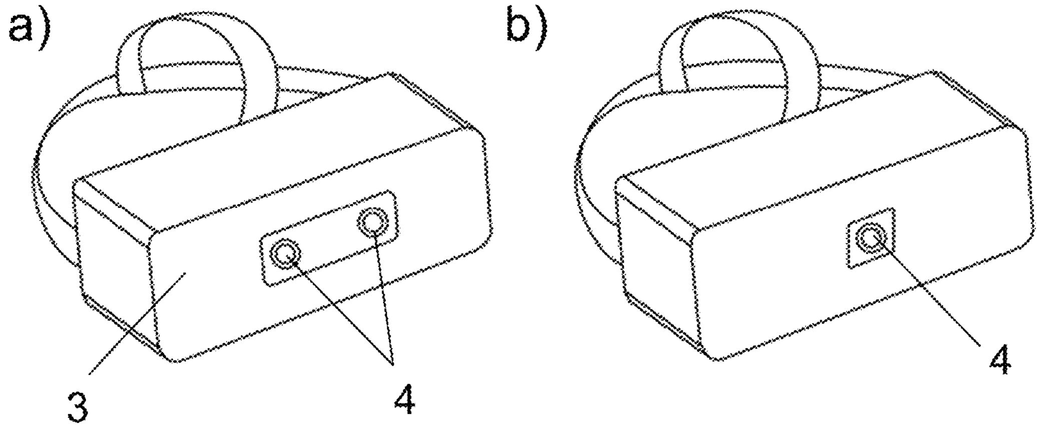
FIG. 2 illustrates two particular embodiments of the viewer, with one (FIG. 2*a*) and two (FIG. 2*b*) cameras incorporated therein.

FIG. 1 shows a preferred implementation of the invention, in reference to an AR/VR system designed for detecting an object (1) on which a user acts by means of a tool (2), sensitive to the movement exerted by the user on same and which must also be detected by the system. The object (1) generally has a larger size than the tool (2). The user wears an AR/VR viewer (3) which provides a field of view within a space comprising the object (1), the tool (2), and the vicinity thereof. Said viewer (3) preferably comprises a first optical means (4) of information acquisition (mainly image, in this embodiment), in particular, one or more cameras (shown in FIG. 2). However, in other embodiments of the invention the first optical means (4) of acquisition can be installed or disposed on other elements (for example, on a tripod or similar support), provided that they allow providing a general perspective of the object (1) for the information/image acquisition thereof.

The system further comprises a processing unit (5), which has the hardware/software means needed to receive the information, for example, the images acquired from the AR/VR viewer (3) and/or from the tool (2). Furthermore, said processing unit (5) allows the storage of all the information associated with the simulation, to be able to subsequently review or analyse same.

The main advantage of the invention is that the tool (2) itself comprises a second optical means (6) of information acquisition (in particular, in FIG. 1 said means comprise an endoscopic camera). Furthermore, there are placed on the object (1) a plurality of optical markers (7, 8) which, in turn, comprise first optical markers (7) which allow tracking with the first optical means (4), and second optical markers (8) which allow tracking through the second optical means (6) incorporated in the tool (2). In different embodiments of the invention, the first markers (7) and the second markers (8) can have the same or different shapes or properties, and they can also partially or completely coincide.

In the preferred embodiment of FIG. 1, the first markers (7), visible from the viewer (3), have a larger size than the second markers (8) specifically designed for being visible from the second optical means (6). Both the first markers (7) and the second optical markers (8) are encoded with optical information suitable for acquisition by the first means (4) and/or the second means (6), and said optical information can be of any of these types: encoded labels, QR codes, images, LEDs, characters, or any other source of information susceptible to optical recognition.

In FIG. 1, the object (1) is a T-shaped part made of PVC (simulating a welding part) and the tool (2) is a welding torch. However, in other preferred embodiments the object (1) can be any type of part, a canvas, or a body; and said tool (2) can be an industrial paint sprayer, an artistic painting tool, a scalpel, a screwdriver, haptic gloves, etc. In general, the tool (2) is smaller than the object (1), so it is an element which is not always clearly observed from the AR/VR viewer (3), either due to occlusions, due to being in a perpendicular position, or due to being especially small. For this reason, the object (1) has a plurality of optical markers (7, 8) which facilitate the detection both from the camera of the tool (2), as well as the detection from the cameras of the AR/VR viewer (3).

The processing unit (5) is configured to receive the images acquired by the first means (4) and/or the second means (6), processing same, and calculating a virtual trajectory. Then, this virtual trajectory is represented by means of a virtual stroke (2') which is plotted in the AR/VR viewer (3), said virtual stroke (2') being related to the real trajectory travelled by the tool (2). Thus, the system allows tracking and representing the interaction of the user with the object (1) even at points which do not belong to the field of view of the viewer (3). Therefore, the images of all the cameras of the system (including the camera of the viewer (3) and the camera of the tool (2) itself) reach the processing unit (5), which images are processed for detecting the markers (7, 8) and thus estimating the localisation of the different elements of the system. The processing unit (5) can be connected in a wired manner to the rest of the elements of the system, or said connection can be wireless.

Figure 3:
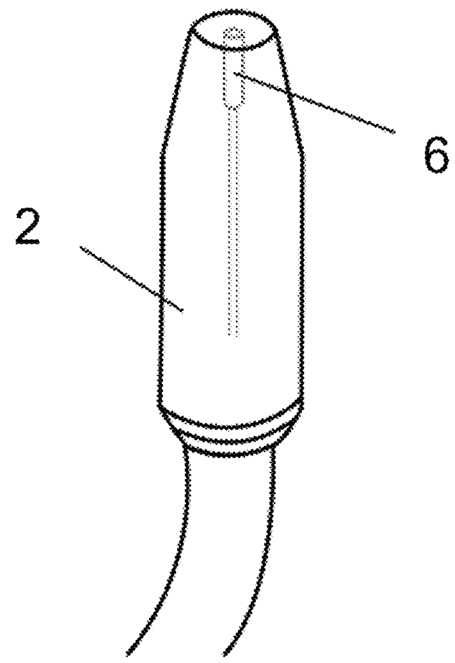
FIG. 3 shows a detail of the tool, where it can be seen how the endoscopic camera is disposed inside same.

FIG. 3 illustrates in greater detail the tool (2) consisting of a welding torch, as shown in FIG. 1, having incorporated an endoscopic camera housed therein.

Figure 4:
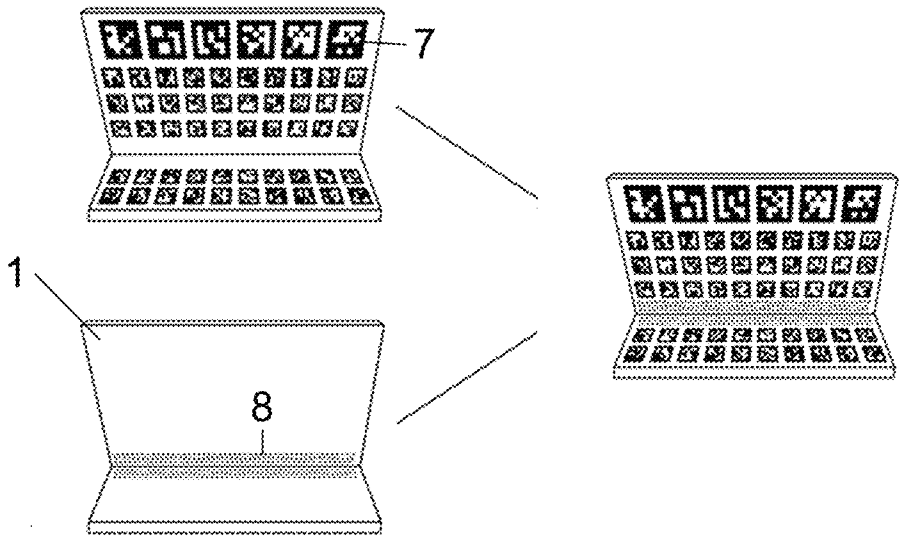
FIG. 4 represents the two types of optical markers disposed on the object. The largest markers are especially designed for being observed from the AR/VR viewer, whereas the smallest markers are mainly used by the tool.

FIG. 4 represents the first optical markers (7), optimised for the AR/VR viewer (3), and the second markers (8), designed specifically for being viewed by the tool (2). It should be noted that, in the particular embodiment of the invention focusing on welding, the second markers (8) are located in the attachment of the object (1) where the application of a welding consumable is simulated. Since in such case it is intended to be able to assess the quality of the simulated weld through the virtual path and the virtual stroke (2'), the second markers (8) need to be smaller and closer together to have a higher resolution and to facilitate the tracking by the processing unit (5). Furthermore, the second markers (8) need not be very large, since the tool (2) preferably works very close to the second markers (8).

Figure 5:
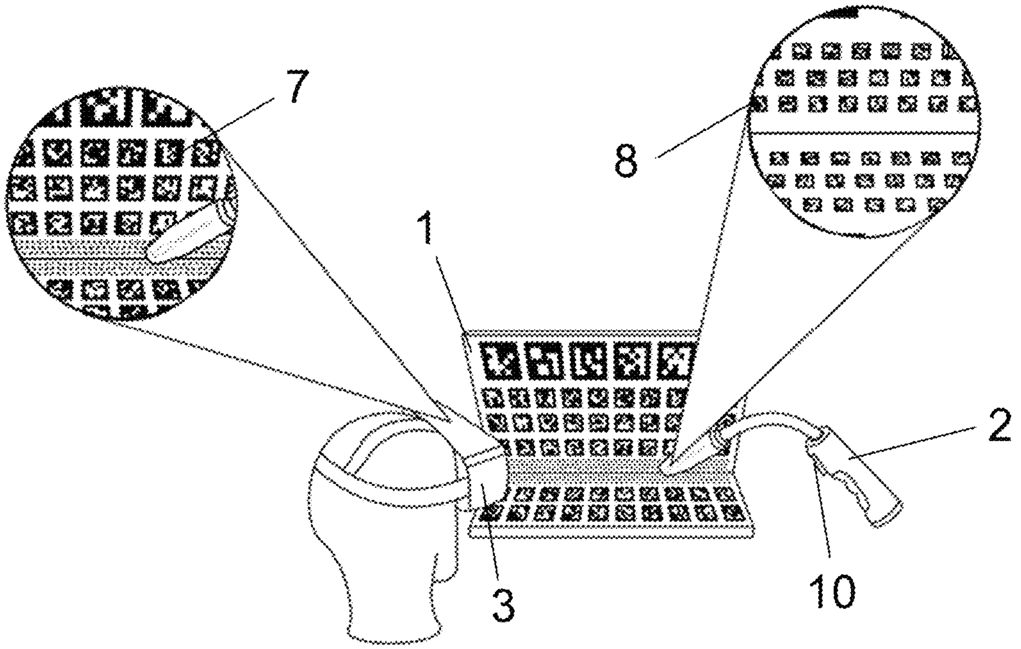
FIG. 5 represents two viewpoints of the optical printed markers on the object, from the camera(s) of the viewer and from the camera of the tool.

FIG. 5 shows the different viewpoints of the different cameras: the camera of the AR/VR viewer (3) locates the first optical markers (7) whereas the camera of the tool (2) observes the second optical markers (8). The first markers (7) for estimating the position from the AR/VR viewer (3) must be visible from same, such as those which are already used in current systems. The possibility of occlusions, which must be visible from a greater distance mayor, etc., must be taken into account. The second markers (8) for estimating the position from the tool (2) must be visible from the camera of said tool (2). For example, if the tool (2) is to work at a distance very close to the part, the optical markers (7, 8) must have a reduced size in order to be visible. The optical markers (7, 8) of the object (1) will also depend on the application: they can be printed markers, retroreflective spheres, LEDs, etc. However, they must allow knowing the position of the tool (2) from the AR/VR viewer (3) using the object (1) as an intermediary. In the case of FIG. 1, where the system emulates a case of welding using square optical markers (7, 8), the tool (2) is used from a close distance. To this end, the object (1) will have a series of second optical markers (7) that are discretionally small for being detected from the tool (2) and first markers (8) having a larger size for being detected from the AR/VR viewer (3). In any case, this separation between the optical markers (7, 8) does not have to be strict. The same markers (7, 8) could be used for both estimations, from the tool (2) and from the viewer (3), if the application allows it.

Figure 6:
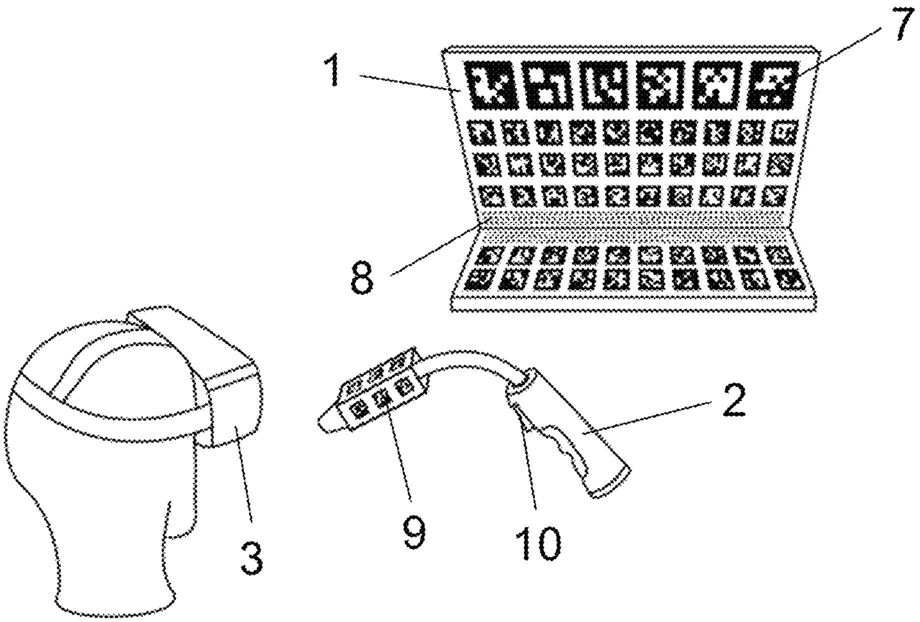
FIG. 6 illustrates a particular embodiment of the tool comprising third optical markers to facilitate the localisation thereof. Likewise, the tool has an ergonomic grip and a trigger that can be comfortably actuated by the user.

FIG. 6 illustrates another even more advantageous embodiment of the invention, wherein the tool (2) further comprises third optical markers (9) and an actuator (10), in particular a trigger, so that it can be comfortably controlled by the user. The third optical markers (9) placed in the tool (2) itself allow the latter to be detected from the AR/VR viewer (3) when the tool (2) is not observing its work area (i.e., when it is not facing the second optical markers (8), the smallest ones in this case). This would be equivalent to the standard detection of tools in AR/VR systems. In the case of a welding simulation, the actuator (10) allows emulating the application of a welding consumable in such a way that the time and the force with which said actuator (10) is operated allows modulating the amount of consumable. In such case, the virtual stroke (2') includes information not only about the real space positions travelled by the tool (2), but also the force and the duration of the pushing applied on the actuator (10). Then, as a result of the fact that the processing unit (5) also stores all the information associated with the weld made by the user, it can be evaluated at a later time (either using the main screen of the AR/VR viewer (3) or additional graphic representation means, such as another monitor), which is useful when the simulator is used for educational purposes. In this sense, can be recorded the points of the virtual trajectory where it has remained for too much time or an excessive amount of consumable has been applied.

Figure 7:
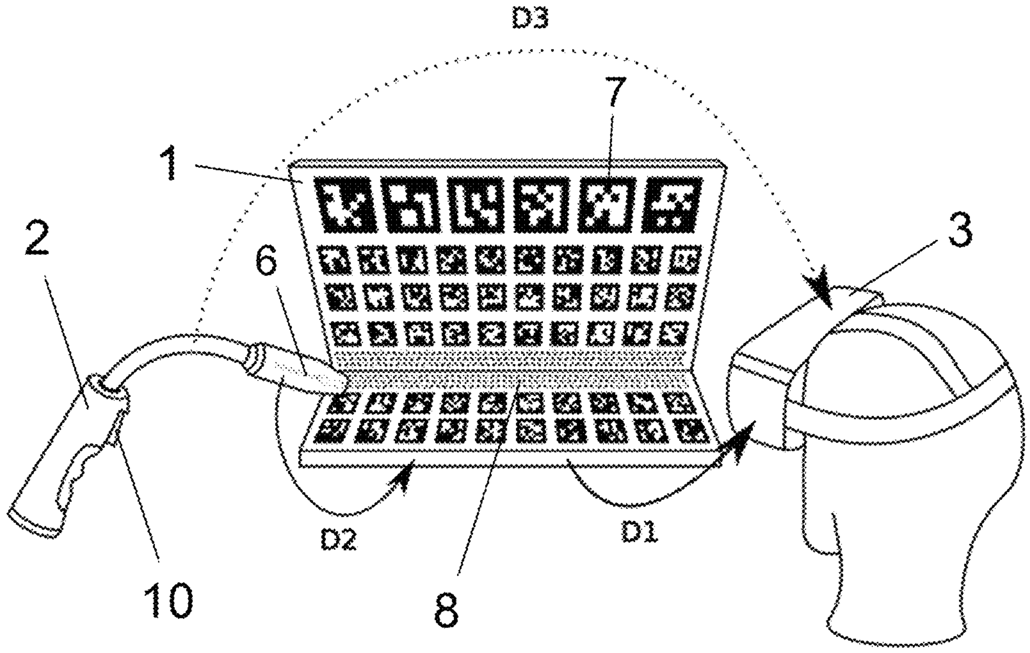
FIG. 7 shows the concatenation of the transformations of the 3D rigid transformation matrices (D1, D2, D3), including information about the rotation and translation of the different elements of the system (tool, object, and viewer) to facilitate the localisation thereof.

As a result of the fact that the tool (2) itself comprises the second optical means (6) of information acquisition, the invention has the following advantages:

- It allows positioning the tool (2) with respect to the object (1) independently of the position of the viewer (3).
- The estimation between the tool (2) and the AR/VR viewer (3) is not affected by the viewpoint of the viewer (3).
- Greater precision can be achieved because the tool (2) is generally closer to the object (1) than the AR/VR viewer (3) and has fewer objects or no object occluded between them.
- If the object (1) is detected from the viewer (3), the position of the tool (2) with respect to the viewer can be known by concatenating the rigid transformation matrices of the different elements: tool (2), object (1), and AR/VR viewer (3). Therefore, the tool (2) in AR/VR can still be shown, although it is not detected directly from the viewer (3). This is illustrated in FIG. 7, in which D1 is the transformation needed to proceed to detection of the object (1) with respect to the AR/VR viewer (3), D2 denotes the transformation associated with the detection of the object (1) with respect to the tool (2); whereas D3 is the concatenation of D1 and D2 and allows the detection of the tool (2) with respect to the AR/VR viewer (3).
- If the tool (2) cannot be located with respect to the object (1), as in the case where the tool (2) exits the field of view of the AR/VR viewer (3), this could continue to be detected with respect to the viewer (3) provided that said tool (2) includes the third optical markers (9), as is done in current AR/VR systems.

The main limitation of the proposed system is that the positioning between the tool (2) and the object (1) can only be estimated when the tool (2) is oriented facing the object (1). However, in many applications it is common for the tool (2) to be observing the object (1) for a large part of the process or it is at this time when greater precision and robustness are needed. For example, in the event that the invention is used as a welding simulator, the precision and robustness in the localisation of the tool (2) is needed when welding is being performed and the torch is facing the object (1). For the rest of the time it may be of interest for the tool (2) to be detected in order to show information on the screen of the AR/VR viewer (3), but it is not critical for the simulation. In any case, when the camera of the tool (2) is not observing the object (1), the tool (2) could continue to be detected by means of the cameras of the viewer (3) as is done in current systems, provided that the tool (2) also includes the third optical markers (9).

In reference to the type of camera comprised in the tool (2), it depends on the type of application and the requirements thereof. For example, some considerations which could be taken into account are:

- If the tool (2) is used from a short distance, a camera with a reduced focal length will be necessary.
- If the camera is to move quickly, it will be necessary to use cameras with a higher refresh rate to avoid motion blur.
- If the tool (2) is small, a camera with a reduced size (for example, an endoscopic camera) can be used.
- If the tool (2) is to be wireless, a wireless camera system could be used.

For each application there will be a design process in which to decide on the best type of camera for the tool (2), and where it will be placed, as well as the best design of optical markers (7, 8) for the object (1). The objective of this design is to optimise the visibility of the optical markers (7, 8) from the tool (2) while at the same time enabling detection of the object (1) from the AR/VR viewer (3).

Another important aspect to be mentioned is the calibration of the system, in particular, the cameras. Since the estimation is independent of the AR/VR viewer (3), the calibration requirements for the cameras in the viewer (3) are not so demanding because the precision and resolution of finer details are obtained as a result of the camera incorporated in the tool (2) itself. However, it is necessary to perform a more thorough calibration of the camera of the tool (2). Like with any optical detection system, this calibration features two parts:

- Intrinsic calibration: focal length, optical centre, and distortion parameters of the camera.
- Extrinsic calibration: relative position of the camera with respect to the tool (2). In other advantageous embodiments of the invention, the second optical means (6) of information acquisition comprises a plurality of cameras configured to provide a stereo system, a multi-view system, or the like, and to thus provide greater precision and/or a larger work area of the tool (2).

In other embodiments of the invention, elements and advantages of several of the different preferred embodiments mentioned above are combined.

Another object of the invention relates to the process for estimating the position between AR/VR viewer (3) and tool (2), which will be denoted as P3. To this end, the position between AR/VR viewer (3) and object (1), hereinafter referred to as P1, as well as position P2, in reference to the position between the tool (2) and the object (1), must be obtained. The simplest case of said process occurs when the tool (2) lacks the third optical markers (9). In such case, each iteration (the duration of which is defined by the update time of the information set by the user) comprises performing the following steps (in any technically possible order):

- Image capture from the first optical means (4) of information acquisition;
- If the first optical markers (7) have been detected, calculation of P1 from the positions of said first optical markers (7).
- Image capture from the second optical means (6) of information acquisition;
- If the second optical markers (8) have been detected, calculation of P2 from the positions of said second optical markers (8).
- If P1 and P2 have been calculated, both positions are combined to calculate P3, which allows locating the position between AR/VR viewer (3) and tool (2).

In alternative embodiments, the tool (2) comprises the third optical markers (9) and the process for estimating the transformation D3 comprises, in addition to the steps indicated in the above process, performing the following steps:

If P3 could not be estimated from the steps of the above process (for example, due to occlusions) or if the localisation is to be refined by means of the use of the third optical markers (9):

a) The third optical markers (9) are detected by the first optical means (4) of information acquisition.

b) Estimate or optimise position P3 using said acquired information (image).

If any of positions P1, P2, or P3 could not be obtained (due to occlusions, etc.), the missing position is estimated from the combination of the other two.

In preferred embodiments of the invention, the tool (2) is connected or joined to one or more terminations, the geometry and dimensions of which vary based on the specific application for which it is used. Preferably, the terminations are used in an AR/VR system which simulates a welding process, although they are also suitable for other applications (painting, etc.). The termination is adapted for housing the second optical means (6) and additional electronics.

Figure 8:
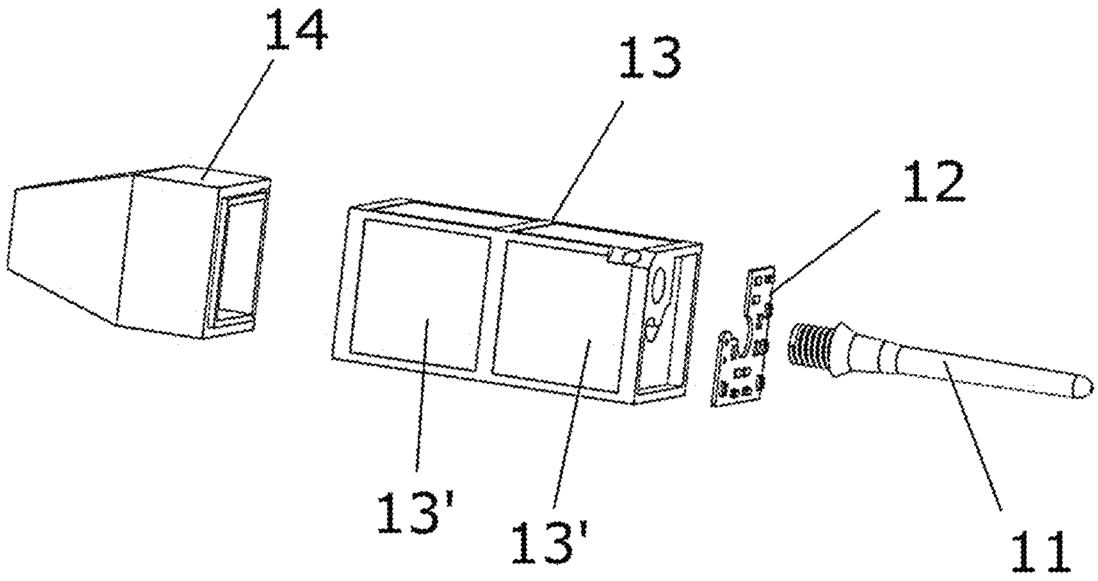
FIG. 8 illustrates an exploded view of a termination for the tool which simulates a welding electrode.
Figure 9:
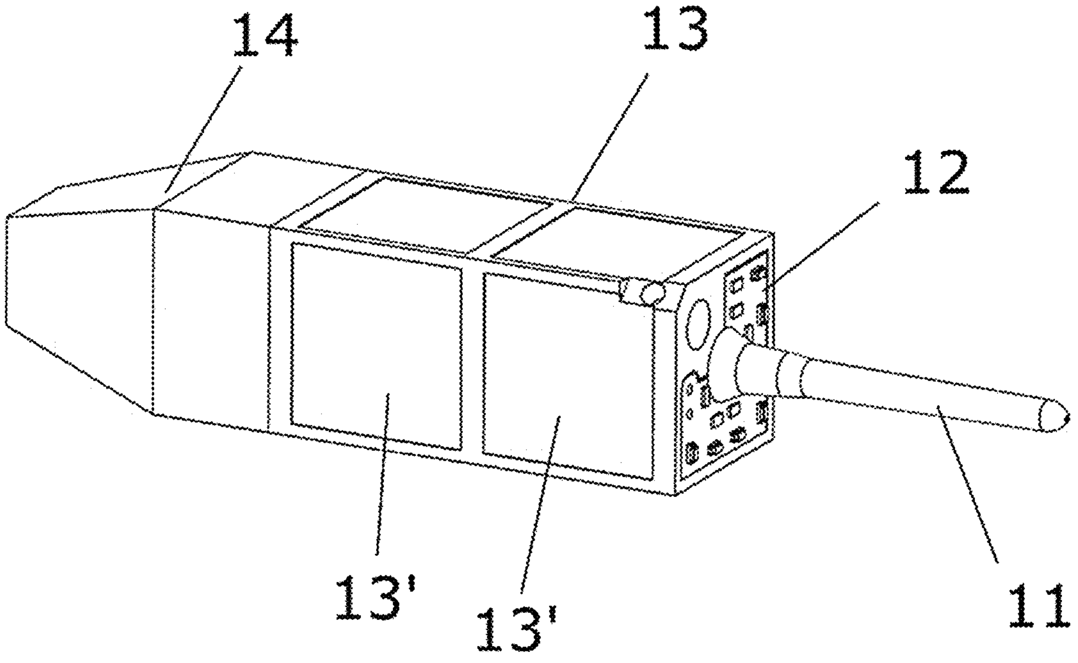
FIG. 9 shows the same termination of FIG. 8, once assembled and prepared for being disposed on the tool.

In a particular embodiment shown in FIGS. 8 and 9, the termination of the tool (2) comprises:

A front end (11) of the termination, also referred to as tip, is dart-shaped, as is shown in FIG. 8, and is adapted for simulating the termination of a welding electrode.

A printed circuit board (12), or equivalent electronics, which in turn integrates lighting means (preferably of a light-emitting diode, or LED, type). Said printed circuit board (12) provides additional lighting to the first means (4) and to the second means (6) of image acquisition, which facilitates the tracking of the optical markers (7, 8, 9).

A main body (13), adapted for housing the second optical means (6) (for example, the endoscopic camera) of the AR/VR system. The second optical means (6) are fixed by means of a set screw or another similar mechanism to keep them in the correct position inside the main body (13). The main body (13) also comprises one or more gaps for housing the printed circuit board (12). The electronics of the second optical means (6) (the endoscopic camera) and conduits for the passage of the wiring are disposed inside the main body (13).

A rear end (14) or cover in the form of a housing to protect the wiring and the electronics of the tool (2). For example, the cover can be placed at the distal end of the termination, the end farthest away from the tip, and covers the terminals of the second optical means (6). The rear end (14) comprises an opening for the exit of the connection wiring and for the tool (2) (in this case, a filler rod).

In certain embodiments of the invention, the assembly of the termination of FIG. 9 is performed using adhesive material and creating a permanent attachment, to prevent it from being easily disassembled. In even more preferred embodiments, the termination also comprises optical markers (7, 8, 9). For example, one or more optical markers (7, 8, 9), such as markers QR, can be placed on one or more faces (13') of the surface of the main body (13) and/or of the cover.

Figure 10:
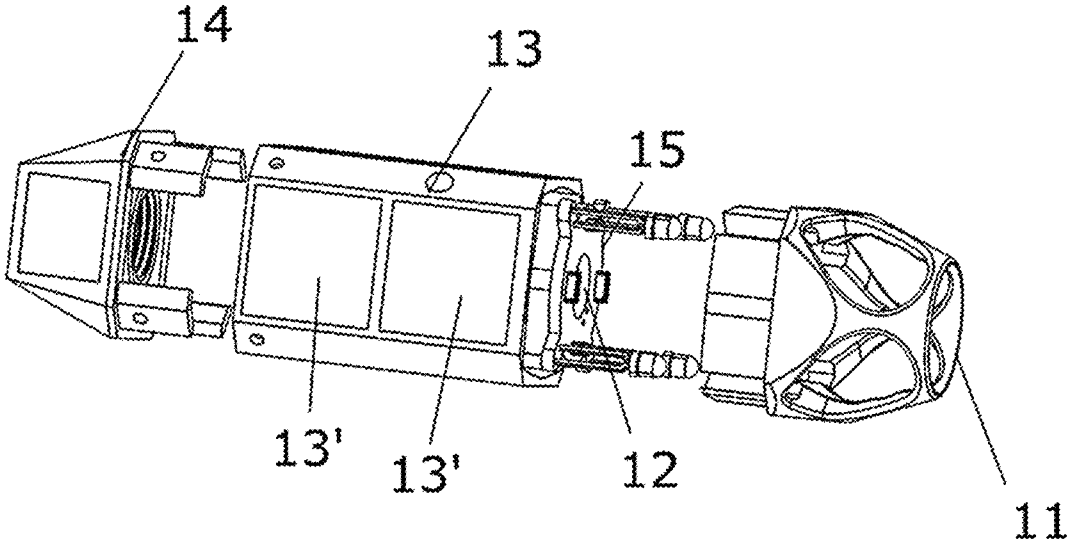
FIG. 10 corresponds to an exploded view of a termination for the tool which simulates a MIG nozzle.
Figure 11:
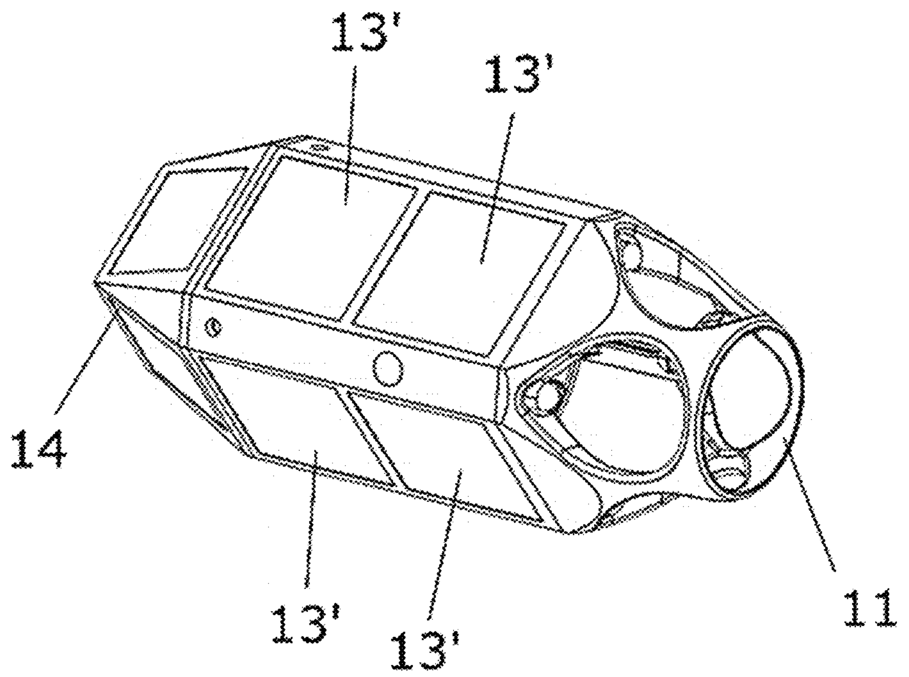
FIG. 11 represents the termination of FIG. 10, once assembled and prepared for being disposed on the tool.

Another example of a termination for the tool (2) (in this case, a MIG torch) can be seen in FIGS. 10-11, which is suitable for simulating a MIG (metal inert gas) nozzle. This termination comprises:

A front end (11) or tip which simulates a MIG nozzle, and which is located in the front part of the termination.

A printed circuit board (12), with lighting means (preferably LED), to provide additional lighting. The printed circuit board (12) comprises a perforation or conduit for housing the second optical means (6) (the endoscopic camera).

A main body (13), which is assembled screwed to a rear end (14) or cover located in the rear part of the termination, houses the second optical means (6) and the printed circuit board (12). The main body (13) also has gaps for housing the LED printed circuit board (12) which provides extra lighting to the first optical means (4) and to the second optical means (6). One or more optical markers (7, 8, 9), for example, a QR or the like, can be placed on one or more faces (13') of the surface of the main body (13) and/or of the rear end (14).

The cover, located in the rear part of the termination, comprises an opening for a thread. Said cover is assembled screwed into the neck of a MIG torch, which acts as the tool (2).

In the exemplary embodiment of FIGS. 10-11, the endoscopic camera is fixed by means of a set screw or mechanism similar which prevents the rotation thereof. The assembly of the main body (13) to the rear end (14) or cover is preferably done by means of set screws. The attachment between the main body (13) and the tip (11) is carried out by means of a press fit.

Figure 12:
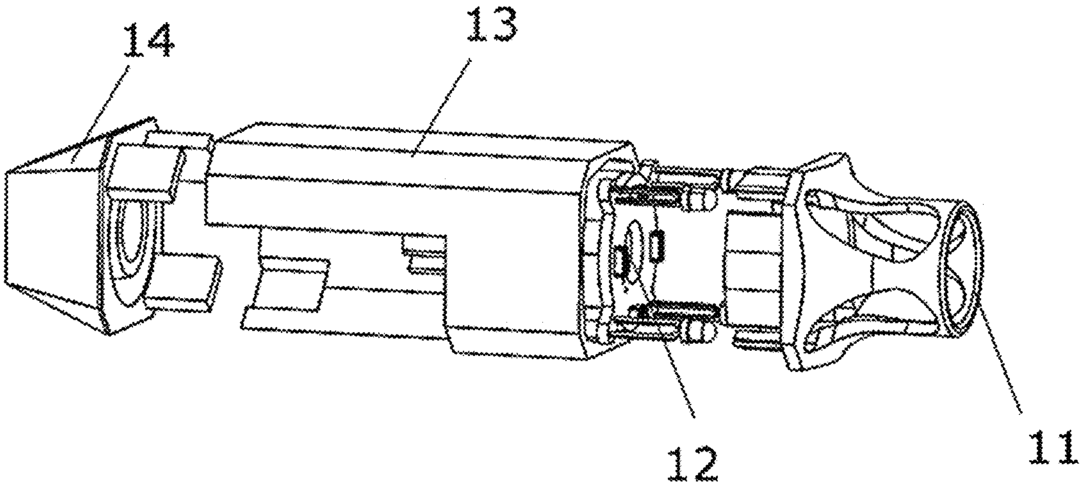
FIG. 12 shows an exploded view of a termination for the tool which emulates a TIG nozzle.
Figure 13A:
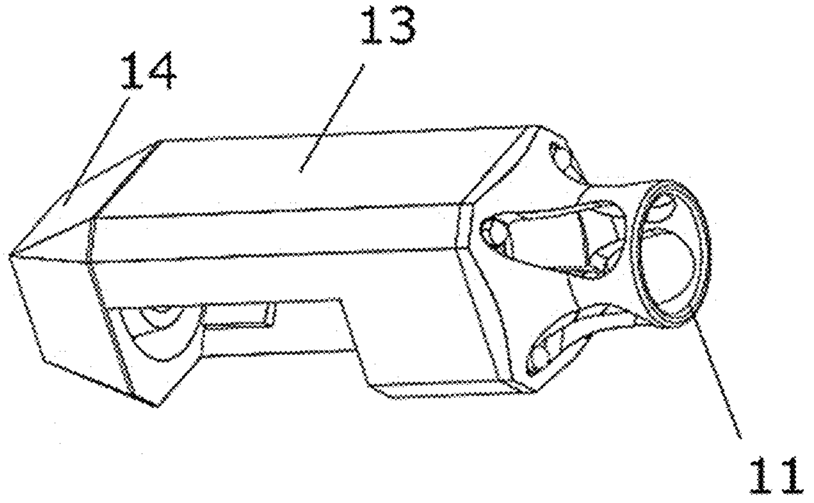
FIGS. 13A-13B shows different views of the termination of FIG. 12, once assembled and prepared for being disposed on the tool.
Figure 13B:
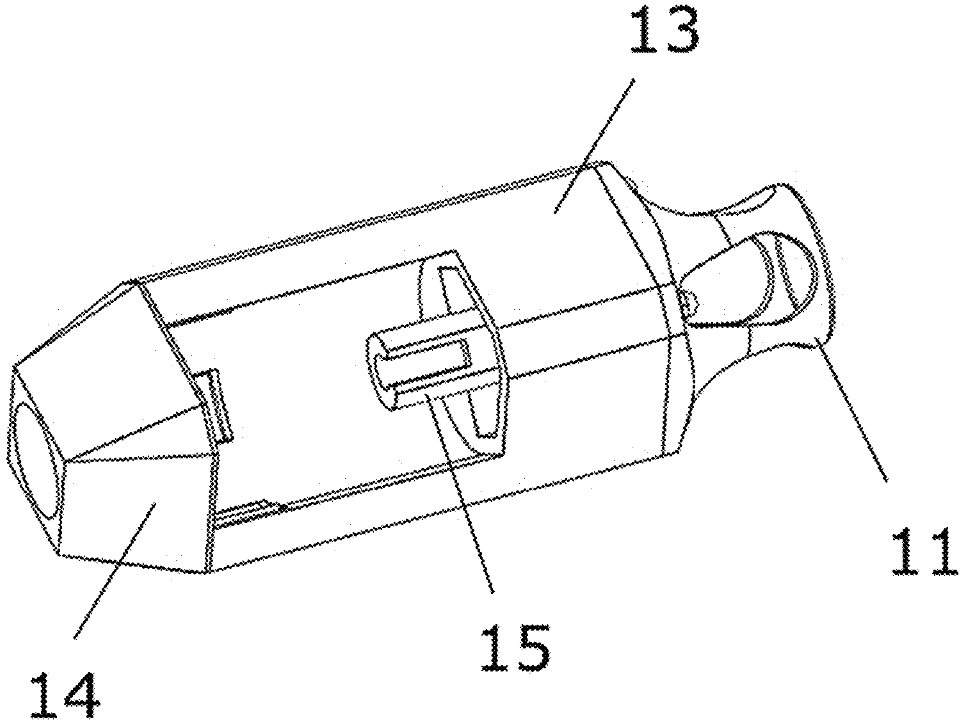

A third example of termination for the tool (12) is illustrated in FIGS. 12, 13A, and 13B, customised for the case where the tool (12) is a TIG (tungsten inert gas) torch. Similarly to the above terminations, this termination comprises:

A front end (11) or tip which simulates a TIG nozzle and closes the termination at the front part thereof.

A printed circuit board (12) with LED lighting, providing additional lighting for the optical means (4, 6).

A main body (13) housing the second means (6) (the endoscopic camera) and the printed circuit board (12).

A rear end (14) or cover in the rear part of the termination and which is coupled to the main body (13) by means of set screws.

A hollow sheath (15) or conduit for housing the endoscopic camera (see FIG. 13B).

The head of the tool (2) (in this case, a TIG torch) is introduced through the rear cover until the tool is housed inside the main body (13). The cover is then screwed on around the head of the TIG torch in order to close the termination assembly. The front end (11) is coupled to the main body (13) by means of mechanical pressure.

Figure 14:
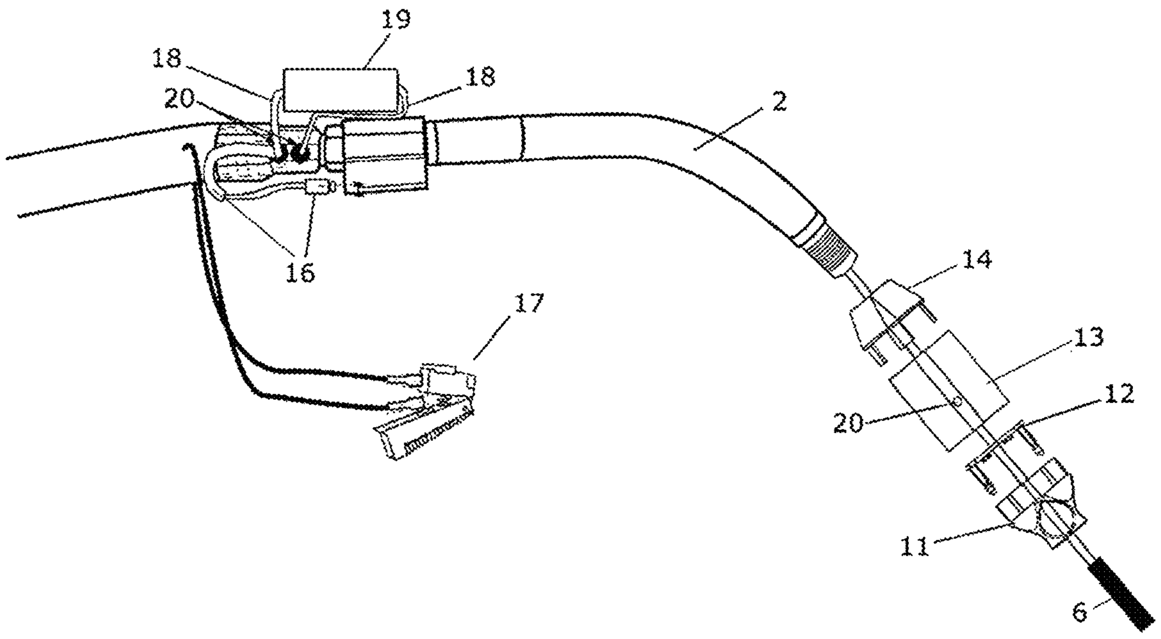
FIG. 14 (not to scale) refers to one of the terminations of the tool. Particularly, the tool emulates a MIG welding torch and the termination comprises an interchangeable tip which can be coupled on the tool.

FIG. 14 corresponds to an embodiment in which the tool (2) is a MIG torch in which a termination like the one shown in FIGS. 10-11 has been incorporated. Namely, it illustrates how the second optical means (6) (the endoscopic camera) are housed in the main body (13) of the termination, protected by the ends (11, 14) of the termination. Preferably, the tool comprises a vibration module (16), which in FIG. 14 is wired and attached to the tool (2). Said tool (2) comprises an actuator (17) or trigger to control the amount of material supplied, as would be done in a case welding real. Furthermore, the tool (2) comprises connectors (18) and wiring for the endoscopic camera, as well as a second printed circuit board (19) comprising the electronics required by the second optical means (6). Lastly, the position of the electronics of the second optical means (6) and of the main body (13) of the termination is ensured by means of fixing elements (20).

With this modular assembly system for assembling the different terminations to the tool (2), a simple assembly of the electronics and/or the integration of the necessary devices corresponding to the endoscopic camera is allowed. It is relevant to observe that all the tips or front ends (11) of the termination, as well as the covers or rear ends (14) of the termination of the tool allow optical markers of any type (for example, QR) or a system of another type to facilitate the detection thereof. The embodiments of terminations shown in FIGS. 8-14 are designed for the case where the tool (2) simulates being a welding torch. These embodiments, together with the endoscopic system, are particularly advantageous in material supply systems, although they can be used in systems of another type which require high work surface precision.

Moreover, the system of the invention considers the case where some of the second optical markers (8) for the second optical means (6) have a very small size, for example, 3 mm×3 mm, so they require a very precise installation (if they are printed markers, the installation of such markers is done by means of adhering same to the object (1)). The inappropriate positioning of the markers negatively affects the detection and the resolution which is obtained with the second optical means (6). When the markers are large (for example, in the case of the first markers (7)) compared with the misalignment or positioning error committed, then this factor does not introduce an important relative error in the detection of the markers. In contrast, if the markers are small (such as the aforementioned second optical markers (8), having dimensions of 3×3 mm) then an error of ±1 mm is very significant at that scale (30% relative error). Therefore, this problem is more evident in the case of the smallest markers, the second markers (8), which are adapted for recognition by the endoscopic camera.

Some of the adherence problems of the markers (7, 8) (for example, in the form of die-cut stickers) comprise horizontal or vertical displacements (for example, according to whether they are in the direction of the weld bead simulated with the system, or on the perpendicular thereof), rotation, uncontrolled deformations in the markers (7, 8) (if these are adhered on the object (1) creases or folds may occur), etc. In a particular manner, displacements and rotations occur most frequently in objects (1) with a tube shape or curved areas, due to the adhering difficulty. These incorrect positioning problems can be seen in the first markers (7), although in these cases the misalignment or the rotation must be significant in order to affect the recognition capacity of the system.

By way of example, FIG. 15A shows the situation where the first markers (7) and the second optical markers (8) are correctly adhered to the object (1), while FIG. 15B represents the case of markers (7, 8) having a vertical and horizontal displacement (which is equivalent to a small anticlockwise rotation). The effect in the first markers (7) is not as pronounced because said markers are larger and, by being detected from a larger distance, positioning errors can be greater. However, in the case of the second markers (8), the effect is very relevant, because the displacement is greater than the size of said second markers (8), which would involve errors in the recognition or localisation of the position thereof on the object (1). Precision in the position of the markers (7, 8) is relevant because they are the positions which are sent to the detection software in the AR/VR system for recognition of the object (1). In this way, the greater the precision there is in the correspondence between the positions which is sent to a detection software module and the positions in which the markers (7, 8) are actually located on the object (1), the greater the precision the AR/VR system has.

FIGS. 16A-16B represent the field of view that encompasses the object (1) and would be seen from the cameras of the AR/VR viewer (3) and from the endoscopic camera of the tool (2). FIG. 16A does not show any inconsistency in the relative position of the markers (7, 8) with respect to the positions which have been sent to the detection software (which are the positions that are seen in the viewer (3)). In contrast, FIG. 16B shows how the positions which were sent to the software (which would correspond with the correct position of the markers (7, 8), according to FIG. 16A) do not coincide with the real positions of said markers (7, 8), due to misalignment and rotation. Therefore, there will be an error in recognition by the AR/VR system.

To overcome the alignment problem of the markers (7, 8) which is observed in FIGS. 15B and 16B, the invention comprises a process for performing a real time mapping of the position of the second markers (8) as they would be observed from the endoscopic camera. In this sense, several images of the object (1) are obtained from several viewpoints and the second markers (8) would thereby be tracked. These images could be obtained by means of the first optical means (4). Optionally, the first markers (7) can be mapped in said images. Advantageously, the real time mapping of the markers is not very intrusive in the operation of the AR/VR system and allows being adapted to any error occurring during the adhesion of the markers (7, 8) to the object (1).

Figure 15:
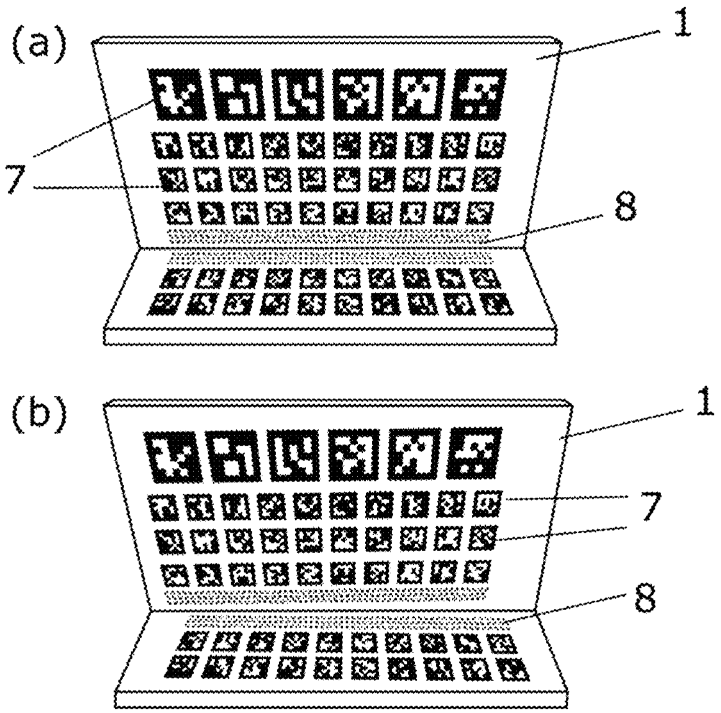
FIGS. 15A-15B illustrate the case of marker misalignment (in this case, die-cut stickers) during adhesion of the markers to the object (in this case, a welding part). This effect has a serious impact when the optical markers are very small.
Figure 16:
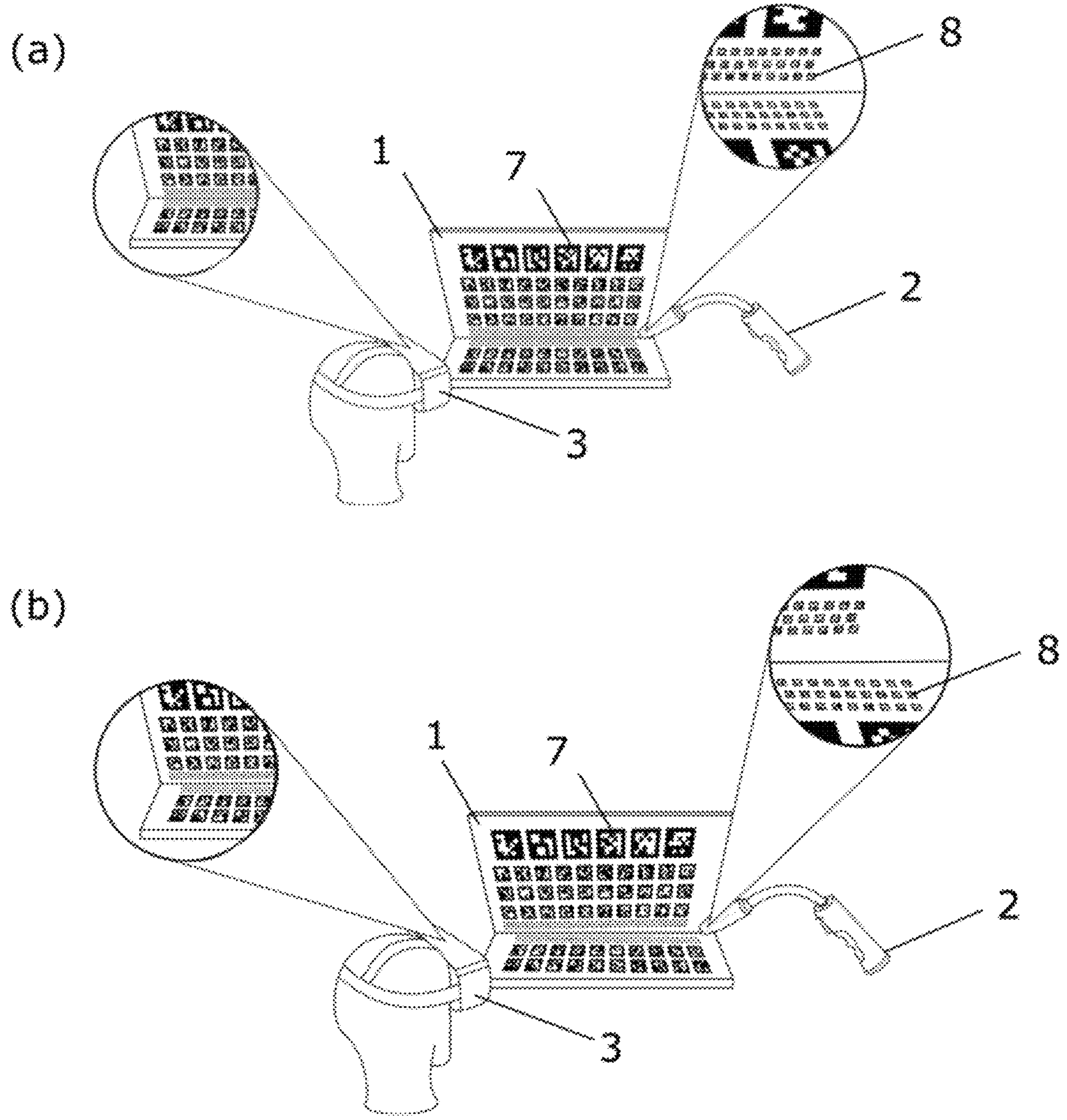
FIGS. 16A-16B correspond, respectively, to the part with adhered markers of FIGS. 15A-15B, as it would be seen from the first optical means (4) of the viewer (3) and from the second optical means (6) of the tool (2).

In FIGS. 15 and 16, the marker mapping process comprises using as the initial map of positions those which are initially known by the software module (FIGS. 15A and 16A), in which the markers (7,8) would have ideally been positioned. However, due to the small size of some of the markers (7,8) it is not always possible to ensure the accuracy of the positioning on the object (1). In these cases, a suitable solution consists of comparing the initial and final map of markers acquired through the optical means (4, 6), wherein the final map comprises the final position of the markers on the object (1). This approach, based on SLAM (particularly, VSLAM) techniques, is used in preferred embodiments of the invention, as will be described below.

Another solution to the problem of the non-correspondence between the positions sent to the detection module for detecting markers (7, 8, 9) and the real positions thereof on the object (1) comprises adding a reference during the manufacture (printing) of the second markers (8) to facilitate the adhering. Alternatively, for custom-manufactured objects (1) (for example, industrial parts) a specific calibration can be carried out (by means of cameras or other sensors for calculating the position of the markers), although this solution lacks repeatability. Additionally, techniques for detecting outliers, for example, RANSAC (random sample consensus), can be incorporated. These techniques allow detecting the markers (7, 8) which are erroneously placed and omit them during detection.

In summary, in order for the localisation of objects with the AR/VR system to be precise, it is important to know with precision the three-dimensional position of these markers (7, 8) on the object (1) with respect to a common reference system. For example, if the object (1) is covered with square markers (7, 8), the coordinates of the markers (7, 8) in the physical object must correspond with the coordinates which provided to the detection software module for detecting markers. If the markers (7, 8) are erroneously placed on the physical object (1), the real coordinates will not correspond with what the detection software module receives. In this case, an error will be propagated in the localisation process, causing deviations and noise.

The maximum positioning error of the markers (7,8) tolerated by the AR/VR system will depend, among others, on the following factors: the specific application to be simulated, the spatial resolution of the means (4, 6) of information acquisition (cameras), and the distance to the markers (7,8).

A particular embodiment of the SLAM (VSLAM) process designed specifically for the system of the invention is described below. Preferably, this process is used in welding simulations in which one or more stickers comprising a plurality of markers (for example, square markers) have been adhered on the object (1). Said system will comprise at least two cameras, specifically the first optical means (4) and the second optical means (6) referred to above. The first means (4) refer to a camera in the viewer (3) of the user, whereas the second (6) means are in the tool (2) itself handled by the user during the simulation, with both being used to acquire images for said SLAM process. In this embodiment, the SLAM map comprises the following information: list of three-dimensional coordinates of the square markers, classification of the markers (for example, indicating to which sticker they belong, if there is more than one; if the sticker is flat or curved, etc.) and the set of keyframes. The main features of the VSLAM process used in the invention distinguishing it from already known VSLAM processes are the following:

The initialisation step is not necessary as the process starts from an initial map with all the markers (7, 8), which is generated together with the design of the part and the manufacture of stickers comprising said markers. It is only necessary to adjust the position of the markers (7, 8) to the disposition thereof on the physical object (1) in the mapping step, as will be seen below.

The localisation step comprises locating the position of the camera in each frame by means of the search for correspondences between the markers observed through the images of the cameras of the system and the markers of the initial map. Preferably the calculation of the position is carried out by means of PnP (Perspective N-Points), which allows estimating the pose of a calibrated camera from a set of N three-dimensional points of known coordinates together with their projections in the image of the camera.

The mapping step is the main novelty that the system of the invention brings to VSLAM. An important difference compared to typical VSLAM versions is that, a priori, markers are neither added to nor deleted from the map. Thus, all markers are known a priori and only their position has to be adjusted according to what the cameras see. Therefore, the current frame and its markers must be compared with the initial markers that were present. In this variant of VSLAM there are a number of criteria for adding a new keyframe:

a) Maximum number of keyframes in the map of markers of the object.

b) A specific number of frames have elapsed since the last keyframe was added.

c) If an error in the localisation of the stickers is detected, then the map can also be updated with a new keyframe.

d) If a minimum quality of detection of each individual sticker is met.

e) If enough different stickers or enough markers are observed for each visible sticker.

f) If a new sticker is visible that was not in the previous key frames.

g) If there is a minimum number of visible stickers.

h) If the distance to previous key frames is greater than a threshold.

In the case of adding a new keyframe, the map is refined using both the new keyframe and all the previous keyframes. Namely, mathematical optimisation is applied to refine the map which takes into account all the observations of the markers in the keyframes (preferably an optimisation known as Structure from Motion is used).

In a preferred embodiment of the VSLAM process, a restriction is added in the optimisation process so that the stickers comprising the markers which are in one plane cannot move out of that plane. For example, the stickers which are in an object (1) with a cylindrical tube shape cannot exit that cylinder and this same logic is applied to any known geometry of the object (1).

In a preferred embodiment of the invention, the VSLAM process comprises the analysis of the images coming from two cameras: the camera of the viewer (3) and the endoscopic camera of the tool (2). In other embodiments of the invention, said VSLAM process can be generalised for a larger number of cameras which had the object (1) in their field of view, thus providing more viewpoints.

In a preferred embodiment of the VSLAM process of this invention, optimisation is performed globally at the level of stickers with markers (7, 8). Therefore, all the markers on the stickers move integrally. Furthermore, the above VSLAM process can be applied for any marker shape (square, circular, etc.) based on the geometry to fit the object (1).

Other alternative embodiments of the VSLAM process of the invention comprise a second optimisation to refine the position of each marker (7, 8) individually, independently of the rest of the markers in the sticker. In the case of objects that are tubes with curved stickers with markers, it is possible for there to be certain deformation in the sticker (for example, because the diameter of the physical part is not exact). In these cases, the markers of the sticker can be divided into different "substickers" at the logical level in order to treat them independently in the optimisation.

In preferred embodiments of the invention, one or more keypoints of the environment of the object (1) are incorporated in the VSLAM process, making the system more robust both in mapping and in localisation.

In certain embodiments of the invention, in the localisation and mapping steps of the VSLAM process performed by the AR/VR simulator, the information acquired with other sensors (inertial sensors, colour sensor with depth or RGB-D information, odometry of a robotic arm, etc.) could be incorporated.

In preferred embodiments of the invention, the AR/VR simulator comprises a vibration functionality of the tool (2) implemented through a vibration hardware and/or software module. Particularly, this functionality can be applied when the tool (2) simulates a welding torch, because the vibrational effect has multiple applications in that context.

One application of the vibration is to provide to the user of the system, in such a way that certain vibration patterns (characterised by a certain frequency, intensity, and duration) inform the user of the performance during the execution of the simulated welding. That is useful when the user is to be informed of aspects such as an inappropriate or excessive application of welding material, an erroneous torch configuration, etc. Some of the variables which can be considered for generating the vibration effects in the tool (2)

are: tension, intensity, gas volume, welding wire feed speed (WFS), working angle, travel angle, travel speed, and contact tip to work distance (CTWD), among others. Preferably, the intensity of the vibration will increase according to the deviation with respect to the ideal value of the variable.

For the case where the AR/VR system is used in welding procedure simulation, another application of vibration is to include in the simulation the physical vibrational effect generated by the drive rolls as would occur in a real welding system, in order to make the AR/VR system more realistic. In this case, the vibration pattern encodes the roll's rotational speed that the real welding torch would have, which in turn depends on several parameters determined by the Welding Procedure Specification (WPS) and the Procedure Qualification Records (PQR). These parameters include: type of welding process, type of wire material, thickness of base material, welding position, wire diameter, transfer type and electrical parameters, among others.

A third application of the inclusion of vibration is that the vibrational energy effects generated by an incorrect welding process can be considered in the simulation, which occurs for example during welding with intermediate transfers that generate changes in the electric arc and wire impact in the molten pool. These types of physical effects are often neglected in other AR/VR simulation systems. In the system of the invention, when a configuration is chosen (e.g., electrical parameters or arc length) that are not synergistic, different effects on material transfer arise. For example, depending on the voltage, wire diameter, wire speed and stick-out, the material transfer to the object (1) can be optimal or irregular. These effects are modelled by taking into account actual measurements on physical welding systems and then extrapolating the data to the simulation.

In particular, the following characteristic transfers can be included in the simulation in the case of GMAW welding:

a) Short-circuit, in which the welding wire hits the molten pool and a voltage spike is generated by a conductivity resistance. This type is very common in the industry and generates welds with lower energy input and with some spatter.

b) Spray, which is one of the most widely used transfers due to its cleanliness, although it generates more energetic effects. The spray is characterised by the fact that the molten material is sprayed into the molten pool.

c) Globular, which is an intermediate situation between short and spray. This type of transfer generates unstable arcs with higher projections.

d) Pulsed arc, which allows the oscillation of the polarity and the dwell time of the wave in which each fringe allows to control the energy and the penetration of the attachment. It is widely used in soft materials with high thermal conductivity (alloys, aluminium).

However, although the vibration-related functionality of the tool (2) has been particularised to the case of welding simulation, such functionality can be incorporated into any type of tool (2), whether or not it comprises the second optical means (6) of information acquisition.

The invention claimed is:

1. An augmented/virtual reality, AR/VR, simulation system operable by a user, wherein said AR/VR system comprises:

an object comprising a plurality of optical markers disposed thereon;

a physical tool suitable for use by the user, said physical tool configured for traveling a real trajectory in a space when used by the user;

an AR/VR viewer;

a first optical device configured for acquiring optical information;

a processing unit communicatively connected at least to the physical tool, the first optical device and the AR/VR viewer;

wherein:

the physical tool comprises a second optical device configured for acquiring optical information;

the physical tool comprises a terminal end;

the plurality of optical markers of the object comprise first optical markers encoded with optical information acquirable by the first optical device, and second optical markers encoded with optical information which is acquirable by the second optical device comprised in the physical tool, wherein the second optical markers define a region of interaction between the physical tool and the object;

the second optical device is arranged at the terminal end of the physical tool such that, for any operative position of the physical tool and the object for which the second optical markers are located within the field of view of the second optical device, said second optical markers are not occluded by the physical tool; and the processing unit comprises software or a hardware device configured to:

acquire the optical information encoded on the first optical markers by the first optical device, acquire the optical information encoded on the second optical markers by the second optical device comprised in the physical tool, process said optical information from the first optical device and the second optical device, based on identifying the first optical markers being observed from the first optical device, and the second optical markers being observed by the second optical device, calculate a virtual trajectory of a simulated tool based on the processed optical information, wherein the virtual trajectory comprises information related to the real trajectory travelled by the physical tool in space when used by the user, and calculate, based on the processed optical information, a simulated interaction result between the physical tool and the object on the region of interaction defined by the second optical markers.

2. The system according to claim 1, wherein the software or the hardware device is further configured to represent a virtual stroke in the AR/VR viewer based on the calculated virtual trajectory of the simulated tool.

3. The system according to claim 1, wherein the physical tool further comprises third optical markers equipped with optical information acquirable by the first optical device.

4. The system according to claim 1, wherein the second optical device comprises an endoscopic camera housed in the physical tool.

5. The system according to claim 1, wherein the physical tool further comprises an actuator connected to the processing unit.

6. The system according to claim 1, wherein at least one of the first optical device and the second optical device comprise one or more cameras.

7. The system according to claim 1, wherein the physical tool further comprises one or more non-optical sensors.

8. The system according to claim 1, wherein the plurality of optical markers comprises at least one of LEDs, QR codes, barcodes, retroreflective spheres, printed markers, and keypoints.

9. The system according to claim 1, wherein:
the AR/VR viewer is housed in a welding mask;
the physical tool further comprises at least one of a welding torch and material supply elements; and
the object comprises a part on which the application of a welding consumable is simulated at a plurality of points delimited by a virtual stroke of the simulated tool.

10. The system according to claim 1, wherein the physical tool further comprises at least one of an industrial paint sprayer, a scalpel, a haptic glove, and a robotic arm.

11. The system according to claim 1, wherein the AR/VR viewer comprises at least one of glasses, a mask, a monitor, and a display of a mobile device.

12. The system according to claim 1, wherein the first optical device is at least partially contained within the AR/VR viewer.

13. The system according to claim 1, wherein the terminal end comprises a detachable portion of the physical tool adapted for housing the second optical device and at least one other portion of the physical tool.

14. The system according to claim 1, further comprising a vibration module adapted for generating one or more vibration patterns of the physical tool.

15. The system according to claim 1, wherein the second optical markers are smaller in physical size than the first optical markers.

16. A process for the calculation of a virtual trajectory with an augmented/virtual reality, AR/VR, simulation system operable by a user, wherein said AR/VR system comprises:
an object comprising a plurality of optical markers disposed thereon;
a physical tool suitable for use by the user, said physical tool configured for traveling a real trajectory in a space when used by the user;
an AR/VR viewer;
a first optical device configured for acquiring optical information;
a processing unit communicatively connected at least to the physical tool, the first optical device and the AR/VR viewer;
wherein:
the physical tool comprises a second optical device configured for acquiring optical information;
the physical tool comprises a terminal end;
the plurality of optical markers of the object comprise first optical markers encoded with optical information acquirable by the first optical device, and second optical markers encoded with optical information which is acquirable by the second optical device comprised in the physical tool, wherein the second optical markers define a region of interaction between the physical tool and the object;
the second optical device is arranged at the terminal end of the physical tool such that, for any operative position of the physical tool and the object for which the second optical markers are located within the field of view of the second optical device, said second optical markers are not occluded by the physical tool;
and wherein the process comprises the following steps:
acquiring optical information encoded on the first optical markers of the object using the first optical device;
acquiring optical information encoded on the second optical markers of the object using the second optical device comprised in the physical tool;
receiving, by the processing unit, the optical information acquired by the first optical device and the second optical device;
processing, by the processing unit, said received optical information, based on identifying the first optical markers being observed from the first optical device, and the second optical markers being observed by the second optical device,
calculating, by the processing unit, a virtual trajectory of a simulated tool based on the processed optical information, wherein the virtual trajectory comprises information related to the real trajectory travelled by the physical tool in space when used by the user, and
calculating, by the processing unit and based on the processed optical information, a simulated interaction result between the physical tool and the object on the region of interaction defined by the second optical markers.

17. The process according to claim 16, further comprising a step of acquiring, by the processing unit, additional information of the physical tool through at least one actuator in the physical tool.

18. The process according to claim 16, wherein the step of calculating a virtual trajectory comprises estimating three positions: a position between the AR/VR viewer and the object, a position between the physical tool and the object, and a position between the AR/VR viewer and the physical tool.

19. The process according to claim 18, wherein the estimation of the three positions in a common spatial reference frame comprises applying a simultaneous localisation and mapping technique for mapping a position of one or more markers of the object in real time.

20. The process according to claim 16, wherein the virtual trajectory is part of a simulated welding technique, a simulated blind welding, a simulated industrial painting, a simulated surgical procedure or a simulated dental procedure.

* * * * *